United States Patent
Komatsu et al.

(10) Patent No.: US 9,885,668 B2
(45) Date of Patent: Feb. 6, 2018

(54) SURFACE INSPECTION DEVICE, SURFACE INSPECTION METHOD, AND PROGRAM

(71) Applicant: Konica Minolta, Inc., Tokyo (JP)

(72) Inventors: Takafumi Komatsu, Osaka (JP); Yoshihisa Abe, Osaka (JP); Wataru Yamaguchi, Osaka (JP); Yosuke Takebe, Osaka (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 15/506,613

(22) PCT Filed: Jul. 21, 2015

(86) PCT No.: PCT/JP2015/070690
§ 371 (c)(1),
(2) Date: Feb. 24, 2017

(87) PCT Pub. No.: WO2016/031434
PCT Pub. Date: Mar. 3, 2016

(65) Prior Publication Data
US 2017/0261439 A1 Sep. 14, 2017

(30) Foreign Application Priority Data

Aug. 29, 2014 (JP) ................. 2014-175407

(51) Int. Cl.
*G01N 21/55* (2014.01)
*G01N 21/95* (2006.01)

(52) U.S. Cl.
CPC .................. *G01N 21/95* (2013.01)

(58) Field of Classification Search
CPC ............ G01N 21/95; G02B 2027/0134; G02B 2027/0156; G02B 27/0093; G02B 27/0172; G02B 27/0176; G02B 27/0179; G02B 5/021
See application file for complete search history.

(56) References Cited

U.S. PATENT DOCUMENTS 7,454,052 B2 * 11/2008 Smilansky ............. G01N 21/94
348/125

FOREIGN PATENT DOCUMENTS

JP 2012-076281 A 4/2012

OTHER PUBLICATIONS

International Search Report issued in PCT/JP2015/070690 dated Oct. 13, 2015 (5 pages).
Written Opinion of the International Searching Authority issued in PCT/JP2015/070690 dated Oct. 13, 2015 (3 pages).

* cited by examiner

*Primary Examiner* — Michael P Stafira
(74) *Attorney, Agent, or Firm* — Osha Liang LLP

(57) ABSTRACT

A surface inspection device includes an opening defining an aperture plane, one or more optical transceivers, and a processor. Each optical transceiver includes a light emitter and a light receiver that are arranged in different directions with respect to the aperture plane when viewed from above a virtual normal line of the aperture plane. The processor acquires detection values from the optical transceivers and calculates an evaluation value of a degree of variation in the detection values.

20 Claims, 12 Drawing Sheets

FIG. 13
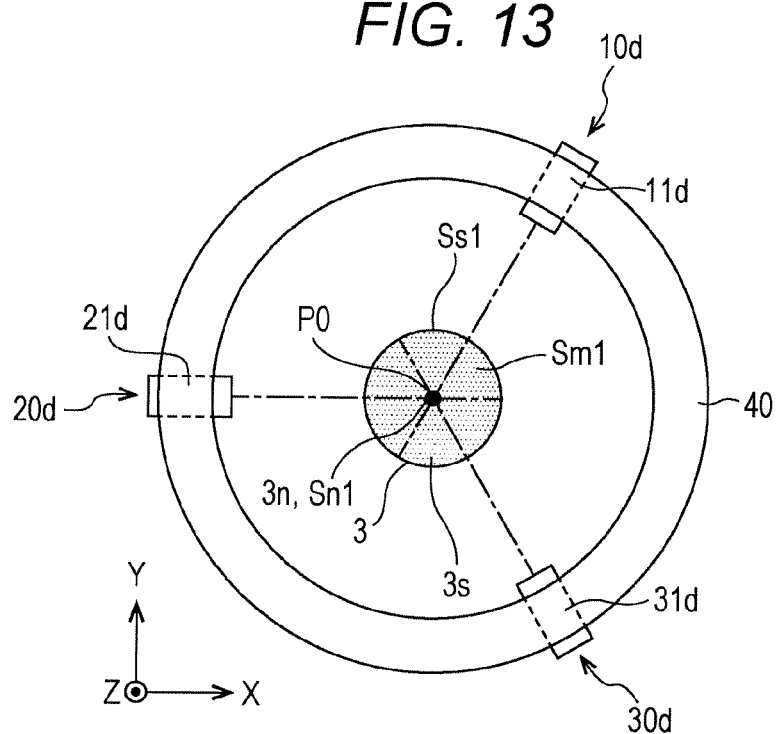
FIG. 14
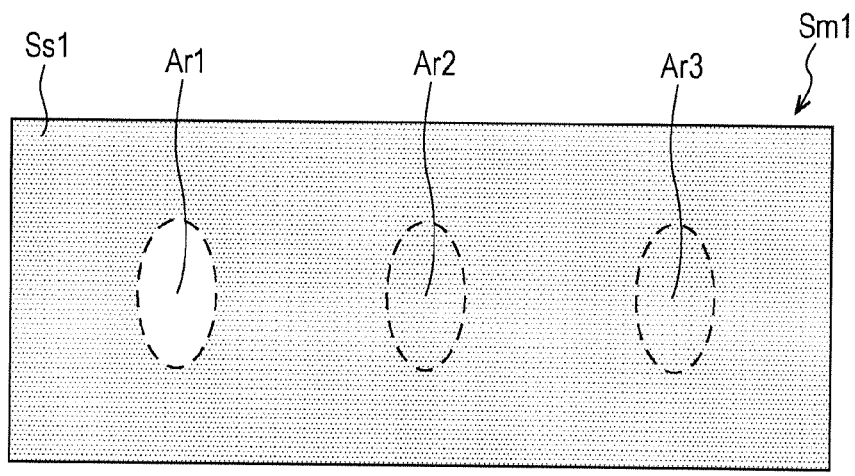
FIG. 15
| UNIT | L* VALUE | ΔL* MAX | DETERMINATION |
|---|---|---|---|
| 10 | 9.71 | 2.14 | WHITE BLURRING FOUND |
| 20 | 11.85 | | |

FIG. 16

| UNIT | L* VALUE | ΔL* MAX | DETERMINATION |
|---|---|---|---|
| 10 | 9.77 | 0.63 | WHITE BLURRING NOT FOUND |
| 20 | 10.40 | | |

FIG. 17

| UNIT | L* VALUE | ΔL* MAX | DETERMINATION |
|---|---|---|---|
| 10 | 9.56 | 1.15 | WHITE BLURRING SUSPECTED OF BEING CAUSED |
| 20 | 10.71 | | |

FIG. 18

| UNIT | L* VALUE | ΔL*_MAX | FIRST DETERMINATION | L*_MEAN | DEVIATION FOR L* VALUE | MAXIMUM DEVIATION FOR L* VALUE | SECOND DETERMINATION |
|---|---|---|---|---|---|---|---|
| 10 | 9.66 | 2.15 | WHITE BLURRING FOUND | 10.53 | −0.87 | 1.28 | WHITE BLURRING FOUND |
| 20 | 11.81 | | | | 1.28 | | |
| 30 | 10.12 | | | | −0.41 | | |

FIG. 19

| UNIT | L* VALUE | ΔL*MAX | FIRST DETERMINATION | L* MEAN | DEVIATION FOR L* VALUE | MAXIMUM DEVIATION FOR L* VALUE | SECOND DETERMINATION |
|---|---|---|---|---|---|---|---|
| 10 | 9.68 | 0.63 | WHITE BLURRING NOT FOUND | 10.07 | −0.39 | 0.24 | WHITE BLURRING NOT FOUND |
| 20 | 10.31 | | | | 0.24 | | |
| 30 | 10.22 | | | | 0.15 | | |

FIG. 20

| UNIT | L* VALUE | ΔL*MAX | FIRST DETERMINATION | L* MEAN | DEVIATION FOR L* VALUE | MAXIMUM DEVIATION FOR L* VALUE | SECOND DETERMINATION |
|---|---|---|---|---|---|---|---|
| 10 | 9.56 | 1.13 | WHITE BLURRING SUSPECTED OF BEING CAUSED | 10.11 | −0.55 | 0.58 | WHITE BLURRING NOT FOUND |
| 20 | 10.69 | | | | 0.58 | | |
| 30 | 10.09 | | | | −0.02 | | |

SURFACE INSPECTION DEVICE, SURFACE INSPECTION METHOD, AND PROGRAM

TECHNICAL FIELD

The present invention relates to a surface inspection device, a surface inspection method, and a program for inspecting a surface of a target.

BACKGROUND ART

For improvement of texture of an interior material for an automobile, a surface of a resin molded article has been typically decorated with a wrinkle pattern of a minute recessed-raised portion called an "embossed portion," for example.

The surface of the resin molded article with the embossed portion has been typically colored by coating. However, in recent years, practical use of an uncoated molded article made of colored resin has been progressively realized for the purpose of reducing a load on environment and simplifying a manufacturing process.

Note that for the resin molded article with the embossed portion, when the surface provided with the embossed portion is observed from a particular direction, a defective appearance called "white blurring" meaning a hazy white appearance might be caused. Such white blurring is often caused on one side of a raised portion forming the embossed portion.

For dealing with occurrence of white blurring as described above, the technique of manufacturing a resin molded article having an embossed portion has been proposed, the embossed portion being configured such that occurrence of white blurring is easily avoided based on a correlation between a shape parameter characterizing the shape of the embossed portion and the degree of white blurring (see Patent Literature 1 and the like).

CITATION LIST

Patent Literature

Patent Literature 1: JP 2012-76281 A

SUMMARY OF INVENTION

Embodiments of the invention may assist in preventing the occurrence of white blurring.

Embodiments of the invention may provide a technique that allows determination of white blurring in an objective manner without variation.

A surface inspection device for inspecting a sample surface according to one aspect includes an opening, a plurality of measurement units, an acquiring section, and a calculation section. These sections may be a processor or other hardware device that acquires data or processes data. The opening defines an aperture plane for measurement. The plurality of measurement units each include a light emitting section and a light receiving section, and are arranged in different directions with respect to the aperture plane when viewed from above a virtual normal line of the aperture plane. The acquiring section is configured to acquire, for each measurement unit, a detection value of the brightness of light emitted from the sample surface in response to light irradiation from the light emitting section via the aperture plane and received by the light receiving section via the aperture plane. The calculation section is configured to calculate an evaluation value of the degree of variation in the multiple detection values acquired for the plurality of measurement units by the acquiring section. A first angle between a first optical path of light from the light emitting section toward the aperture plane and the virtual normal line of the aperture plane, a second angle between a second optical path of light from the aperture plane toward the light receiving section and the normal line, and a third angle between the first and second optical paths are equal among the plurality of measurement units.

A surface inspection method according to another aspect includes steps (a) to (c). At the step (a), a surface inspection device is prepared, which is provided with an opening defining an aperture plane for measurement, which includes a plurality of measurement units each including a light emitting section and a light receiving section and arranged in different directions with respect to the aperture plane when viewed from above a virtual normal line of the aperture plane, and which is configured such that a first angle between a first optical path of light from the light emitting section toward the aperture plane and the virtual normal line of the aperture plane, a second angle between a second optical path of light from the aperture plane toward the light receiving section and the normal line, and a third angle between the first and second optical paths are equal among the plurality of measurement units. At the step (b), a detection value of the brightness of light emitted from the sample surface in response to light irradiation from the light emitting section via the aperture plane and received by the light receiving section via the aperture plane is acquired for each measurement unit. At the step (c), an evaluation value of the degree of variation in the multiple detection values acquired for the plurality of measurement units at the step (b) is calculated.

A program according to still another aspect causes a surface inspection device to function as the surface inspection device that inspects a sample surface according to the one aspect by a control section included in the surface inspection device.

Advantageous Effects of Invention

According to the surface inspection device of the one aspect, white blurring can be determined in an objective manner without variation.

According to the surface inspection method of another aspect, an advantageous effect similar to that of the surface inspection device according to the one aspect is produced.

According to the program of the still another aspect, an advantageous effect similar to that of the surface inspection device according to the one aspect is produced.

BRIEF DESCRIPTION OF DRAWINGS

FIG. 13 is a view of an arrangement relationship among a light emitting region and a plurality of measurement units.

FIG. 14 is a view of an example of a sample surface.

FIG. 15 is a table of inspection results obtained by the surface inspection device according to the first embodiment.

FIG. 16 is a table of inspection results obtained by the surface inspection device according to the first embodiment.

FIG. 17 is a table of inspection results obtained by the surface inspection device according to the first embodiment.

FIG. 18 is a table of inspection results obtained by the surface inspection device according to the second embodiment.

FIG. 19 is a table of inspection results obtained by the surface inspection device according to the second embodiment.

FIG. 20 is a table of inspection results obtained by the surface inspection device according to the second embodiment.

DESCRIPTION OF EMBODIMENTS

Figure 1:
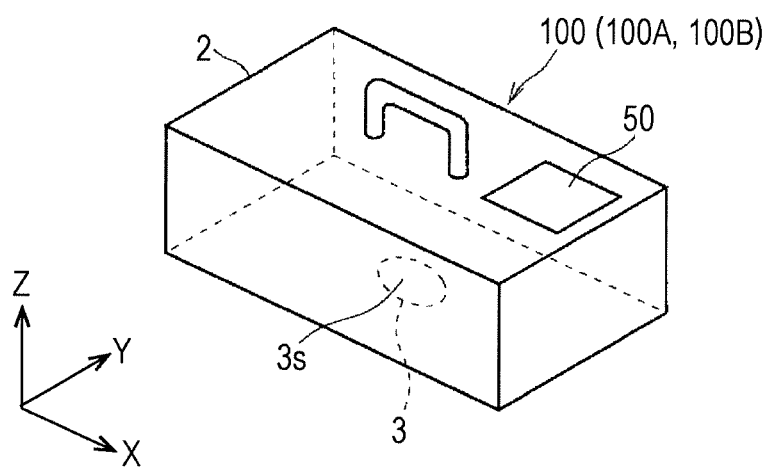
FIG. 1 is a perspective view of an outer appearance common to a surface inspection device according to each embodiment.

Embodiments of the invention will be described below with reference to drawings. Note that the same reference numerals are used to represent elements having similar configurations and functions in the drawings, and overlapping description thereof will not be made below. Moreover, the drawings are schematically illustrated, and the sizes, positional relationships, and the like of various structures in each drawing are optionally changeable. Note that in FIGS. 1, 2, 4 to 7, 10, and 13, a right-handed XYZ coordinate system is employed, in which an extension direction of a normal line $3n$ of an aperture plane $3s$ toward a device body 2 is a Z-direction. Moreover, in FIGS. 3, 9, and 12, a sample Sm1 is illustrated as reference, and the path of light with which a sample surface Ss1 is irradiated and the path of reflected light from the sample surface Ss1 are schematically illustrated using chain lines.

(1) Summary of Surface Inspection Device of Each Embodiment

Figure 2:
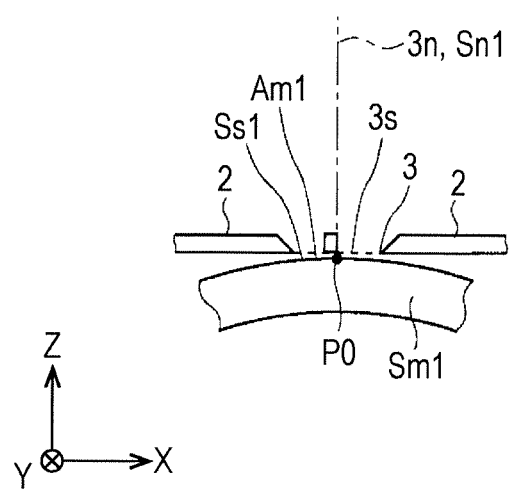
FIG. 2 is a schematic view of an arrangement relationship between a device body common to the surface inspection device according to each embodiment and a sample surface as a measurement target surface of a sample.

FIG. 1 is a perspective view of an outer appearance common to a surface inspection device 100 (100A, 100B) according to each embodiment. Moreover, FIG. 2 is a schematic view for describing an arrangement relationship between the device body 2 common to the surface inspection device 100 (100A, 100B) according to each embodiment and the surface (also referred to as a "sample surface") Ss1 of the sample Sm1 as an inspection target surface.

The surface inspection device 100 (100A, 100B) is a device configured to inspect the sample surface Ss1 of the sample Sm1. The sample Sm1 described herein is, for example, a resin molded article having an embossed portion forming an interior material of an automobile. A main target for inspection by the surface inspection device 100 (100A, 100B) is, for example, occurrence of a defective appearance so-called "white blurring" in the resin molded article having the embossed portion.

As illustrated in FIG. 1, the surface inspection device 100 (100A, 100B) includes, for example, the device body 2 mainly incorporating various configurations. The device body 2 is provided with a measurement opening 3 drilled at a bottom wall and an operation display section 50 disposed on a proper portion of a surface of the device body 2. The opening 3 defines an aperture plane $3s$ for measurement. The aperture plane $3s$ is formed by, for example, a portion of the opening 3 forming an outer surface of the device body 2.

The operation display section 50 includes, for example, a display section configured to visually output various types of information such as an inspection result, and a touch panel type operation switch. The surface inspection device having such a configuration forms, for example, a portable device.

In inspection of the sample surface Ss1 by the surface inspection device 100 (100A, 100B), the device body 2 is disposed such that the opening 3 faces the sample surface Ss1, and a region of the sample surface Ss1 facing the opening 3 is an inspection region Am1, as illustrated in FIG. 2. In this state, the device body 2 is disposed to face the sample surface Ss1 such that the normal line $3n$ of the opening 3 and a normal line Sn1 of the inspection region Am1 are coincident with each other.

(2) First Embodiment

<(2-1) Functional Configuration of Surface Inspection Device>

Figure 3:
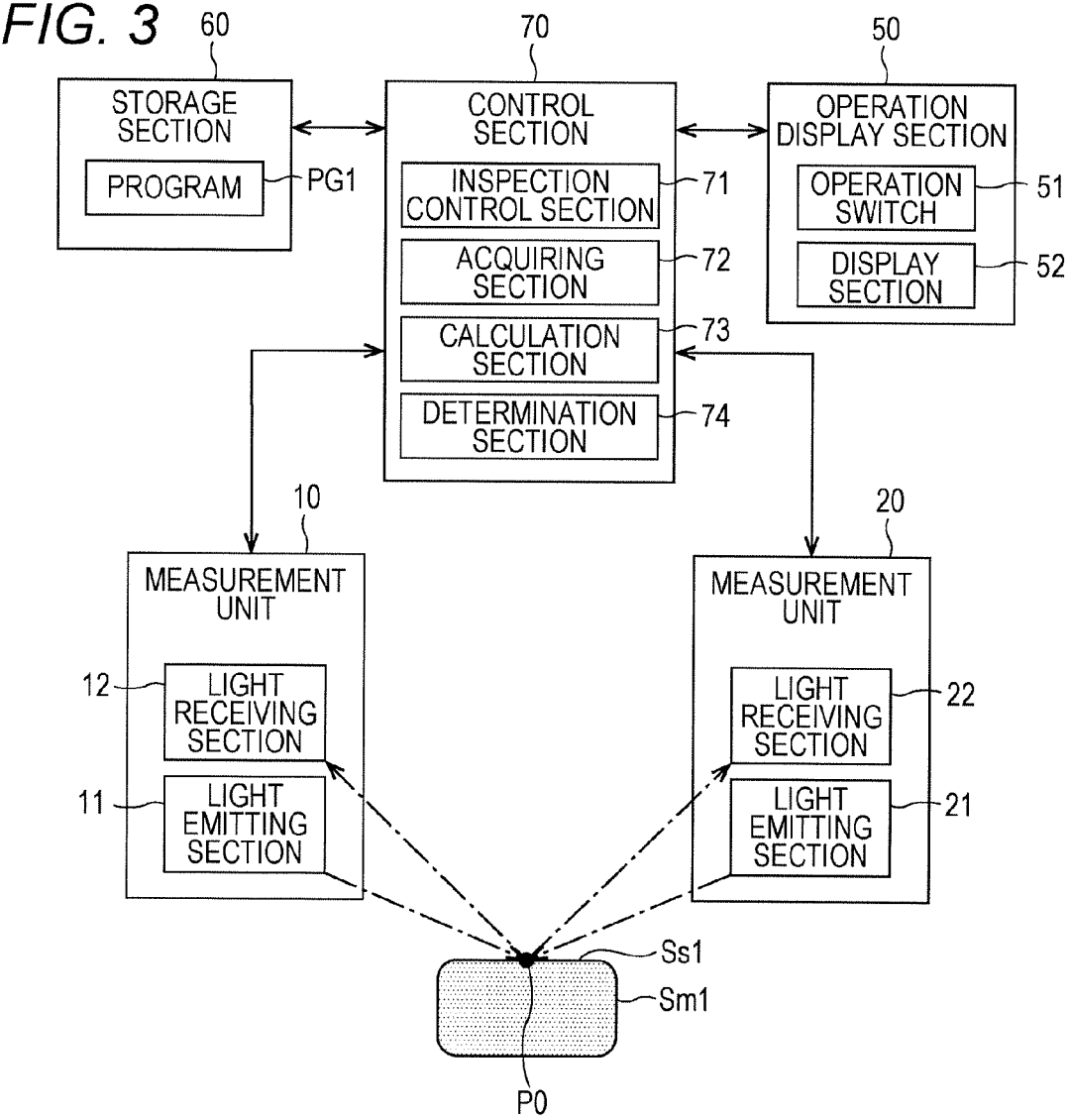
FIG. 3 is a diagram of a functional configuration of a surface inspection device according to a first embodiment.

FIG. 3 is a diagram of a functional configuration of a surface inspection device 100 according to a first embodiment.

The surface inspection device 100 includes a plurality of measurement units 10, 20, an operation display section 50, a storage section 60, and a control section 70. The measurement unit 10 may be an optical transceiver. The measurement unit 10 has a light emitting section 11 and a light receiving section 12, and the measurement unit 20 has a light emitting section 21 and a light receiving section 22. The light emitting section may be a light emitter, such as an optical transmitter, and the light receiving section may be a light receiver such as an optical receiver. The measurement unit 10 and the measurement unit 20 are arranged in different directions with respect to an aperture plane $3s$ as viewed from above a virtual normal line $3n$ of the aperture plane $3s$.

Figure 4:
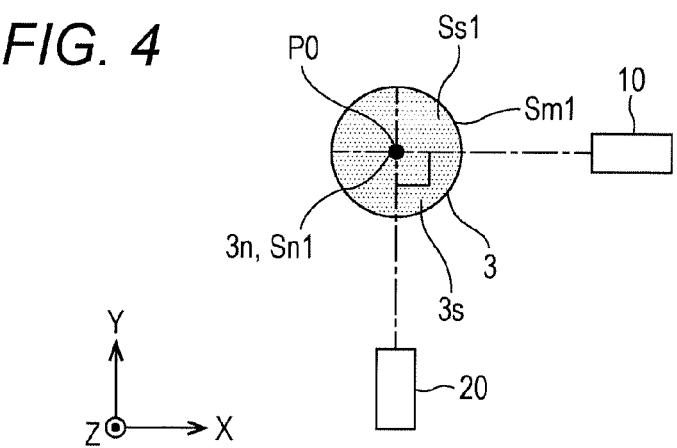
FIG. 4 is a view of a right-angled arrangement relationship between two measurement units.
Figure 5:
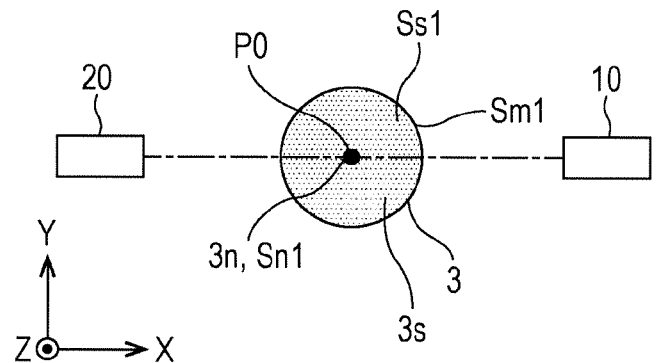
FIG. 5 is a view of a linear arrangement relationship between the two measurement units.

For example, as illustrated in FIG. 4, an aspect is conceivable, in which the measurement unit 10 and the measurement unit 20 are in such a relationship that the measurement unit 10 and the measurement unit 20 rotate from each other about the normal line $3n$ by a predetermined angle (in this example, 90°) set in advance. In light of a characteristic that white blurring is recognizable as viewed from a particular direction, when the predetermined angle is equal to or greater than 90°, a sample surface Ss1 can be evaluated from two directions different from each other to some extent. That is, anisotropy of properties of the sample surface Ss1 can be properly evaluated. This can enhance the accuracy of determination of white blurring. Note that as illustrated in FIG. 5, when the predetermined angle is set to, for example, about 180°, the degree of freedom in a configuration of a device body 2 of the surface inspection device 100 is improved, and the size of the surface inspection device 100 can be reduced.

The plurality of light emitting sections 11, 21 are separately provided apart from each other, and each have a light source configured to emit light such as white light, for example. The light source is provided with, for example, a light emitting circuit configured to perform light emission. In this example, examples of the light source include a xenon flash tube and the like. Moreover, each of the light emitting sections 11, 21 is optionally provided with a regulation plate configured to regulate a light beam, a collimate lens, and the like. For example, the regulation plate is disposed such that an opening of the regulation plate is coincident with the focal point of the collimate lens. A light beam emitted from the light source through the opening of the regulation plate is converted into a parallel light beam by the collimate lens, and then, a measurement point P0 of the sample surface Ss1 is irradiated with the parallel light beam.

The light emitting circuit has, for example, a semiconductor switch element, a drive circuit, a main capacitor, a charging circuit, and a trigger generation circuit. The semiconductor switch element includes, for example, an IGBT and the like. The drive circuit is configured to apply drive voltage to the semiconductor switch element. The main capacitor is configured to apply a high DC voltage of several hundred volts to each electrode of the light source. The charging circuit is configured to charge the main capacitor. The trigger generation circuit is configured to apply a high AC voltage of several tens of thousands of volts to a trigger electrode including a metal wire and the like wound around the light source in close contact with the light source. In this example, in the state in which the semiconductor switch element is turned ON and that the main capacitor applies high DC voltage to the electrodes at both ends of the light source, high AC voltage is instantaneously applied to the trigger electrode via a trigger transformer by a trigger capacitor of the trigger generation circuit. In such a state, the light source emits light in such a manner that DC flows from the main capacitor to the light source.

The plurality of light receiving sections 12, 22 are each a section configured to receive reflected light from the measurement point P0 of the sample surface Ss1. The light receiving sections 12, 22 each have a light detection unit having a photoelectric conversion element configured to convert received light into an electric signal, for example. A spectrometer such as a polychromator is employed as the light detection unit, for example. In the light detection unit, incident light is separated for each wavelength, and spectroscopy data according to the strength of light for each wavelength is output, for example. In the light detection unit, incident light entering through a slit-shaped entrance is dispersed by a concave diffraction grating, and then, is received and converted into an electric signal at a line sensor, for example.

The operation display section 50 has an operation switch 51 and a display section 52. The operation switch 51 is for instructing, for example, initiation of inspection of the sample surface Ss1. The display section 52 includes, for example, a liquid crystal display panel and the like, and is configured to visually output various types of information on an inspection result and the like.

The storage section 60 has, for example, a RAM, an EEPROM, and the like. The storage section 60 is configured to temporarily save data indicating a measurement result, the inspection result, and the like and to store a program PG1 for operating the control section 70.

The control section 70 includes a processor such as a central processing unit (CPU), a memory such as a RAM, and an electronic circuit such as an A/D converter. The control section 70 reads and executes the program PG1 to control operation of each section of the surface inspection device 100, thereby implementing functions of the surface inspection device 100. For example, the control section 70 has, as functional configurations implemented by reading and execution of the program PG1, an inspection control section 71, an acquiring section 72, a calculation section 73, and a determination section 74.

The inspection control section 71 is configured to cause each of the light emitting sections 11, 21 to sequentially emit light according to user's operation of the operation switch 51, thereby causing the surface inspection device 100 to execute inspection of the sample surface Ss1, for example. Moreover, the inspection control section 71 is configured to display, on the display section 52, at least one of a calculation result obtained by the calculation section 73 or a determination result obtained by the determination section 74.

The acquiring section 72 is configured to acquire, for the measurement unit 10, a detection value of the brightness of light (in this example, mainly reflected light) emitted from the sample surface Ss1 in response to light irradiation from the light emitting section 11 via the aperture plane 3$s$ and received by the light receiving section 12 via the aperture plane 3$s$. The light emitted from the sample surface Ss1 may contain fluorescence in addition to the reflected light.

For example, in the light receiving section 12, the electric signal indicating the spectroscopy data according to the strength of light for each wavelength of received light is output from the light detection unit. Then, in the acquiring section 72, spectral reflectance properties are obtained based on the electric signal, and color information (e.g., tristimulus values of an XYZ color coordinate system) on the sample surface Ss1 at the measurement point P0 is obtained based on the spectral reflectance properties. Further, in the acquiring section 72, the color information is converted into color information on an L*a*b* color coordinate system, and in this manner, an L* value is acquired as the detection value of the brightness, for example. The L*a*b* color coordinate system is a color coordinate system standardized by the International Commission on Illumination (CIE) in 1976.

Further, similarly for the measurement unit 10, the acquiring section 72 is configured to acquire, for the measurement unit 20, a detection value of the brightness of light emitted from the sample surface Ss1 in response to light irradiation from the light emitting section 21 via the aperture plane 3$s$ and received by the light receiving section 22 via the aperture plane 3$s$. That is, in the acquiring section 72, the detection value (e.g., the L* value) of the brightness is acquired for each of the measurement units 10, 20. For example, in this example, the separately-provided light emitting sections 11, 12 sequentially emit light, and the detection value of the brightness of reflected light received by the light receiving section 12 in light emission from the light emitting section 11 is acquired, and the detection value of the brightness of reflected light received by the light receiving section 22 in light emission from the light emitting section 21 is acquired. This can realize improvement of an S/N ratio in acquiring of the detection values and device size reduction.

The calculation section 73 is configured to calculate an evaluation value of the degree of variation in the multiple brightness detection values acquired for the plurality of measurement units 10, 20 by the acquiring section 72. Such an evaluation value may include, for example, at least one of a difference or a ratio between the multiple detection values of the brightness. Note that, for example, a value obtained by dividing one of the multiple detection values by the other detection value may be employed as the ratio between the multiple detection values. This can easily determine white blurring.

The determination section 74 is configured to determine the state of the sample surface Ss1 based on the evaluation value calculated by the calculation section 73. In this manner, white blurring can be determined in an objective manner without variation. In the determination section 74, the state of the sample surface is determined by comparison between the evaluation value and a preset reference value, for example. This can easily determine white blurring in the objective manner without variation.

For example, a case may be assumed, in which the evaluation value is a difference (also referred to as a "maximum difference") $\Delta L^*_{MAX}$ between a maximum value $L^*_{MAX}$ and a minimum value $L^*_{MIN}$ of the multiple detection values (the L* values) obtained by the acquiring section 72 and the reference value is 1.2. In this case, when the maximum difference $\Delta L^*_{MAX}$ exceeds, for example, a reference value of 1.2, it is estimated that there is a certain amount of great difference in the brightness of the sample surface Ss1 depending on the direction of irradiating the sample surface Ss1 with light. Thus, it is determined that there is white blurring on the sample surface Ss1. Note that the reference value can be, for example, set according to a sensory evaluation result by together performing calculation of the maximum difference $\Delta L^*_{MAX}$ as the evaluation value obtained using the surface inspection device 100 or a configuration or a simulation similar to the surface inspection device 100 and sensory evaluation on the presence of white blurring by visual checking of the sample surface Ss1. That is, the reference value can be set according to an allowable degree of white blurring. Moreover, the reference value may further include an auxiliary reference value according to the likelihood of white blurring. For example, in the case where the auxiliary reference value is 0.8 and $\Delta L^*_{MAX}$ is greater than 0.8 and equal to or less than a reference value of 1.2, it is estimated that there is a certain amount of difference in the brightness of the sample surface Ss1 depending on the direction of irradiating the sample surface Ss1 with light. Thus, it is determined that white blurring is suspected of being caused on the sample surface Ss1.

<(2-2) Configuration of Measurement Unit>

Figure 6:
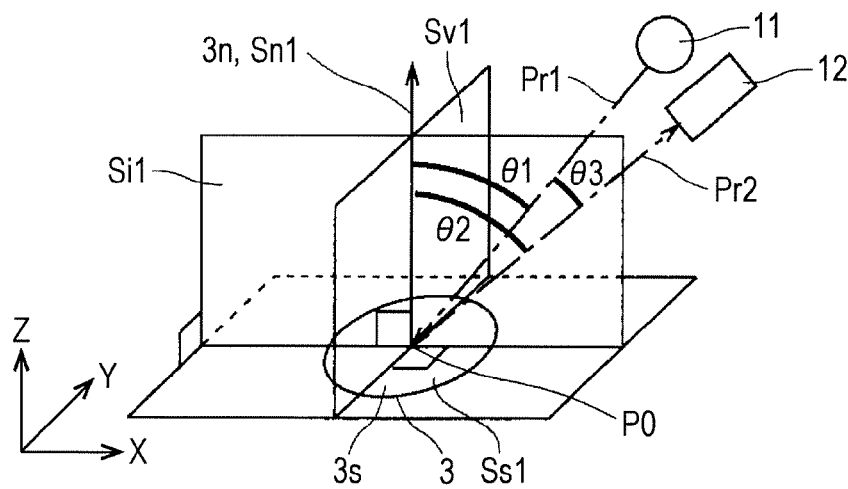
FIG. 6 is a view of an arrangement state of a light emitting section and a light receiving section in the measurement unit.
Figure 7:
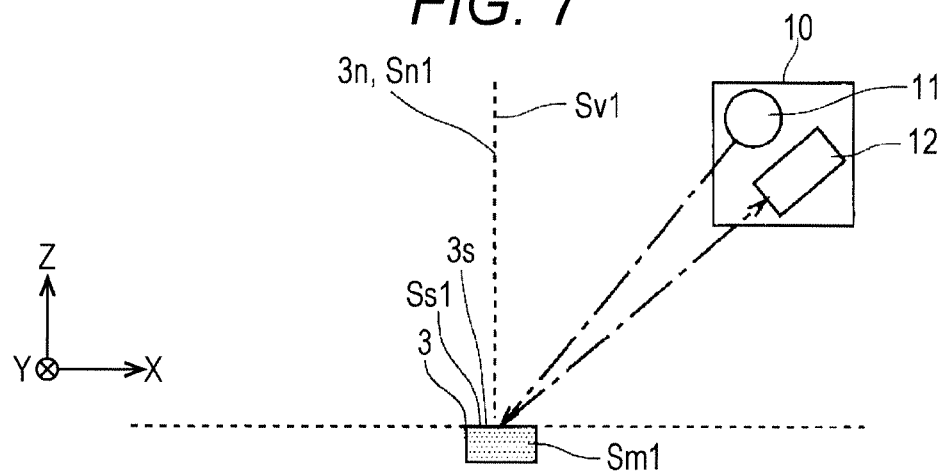
FIG. 7 is a view of the arrangement state of the light emitting section and the light receiving section in the measurement unit.

FIGS. 6 and 7 are views for describing an arrangement state of the light emitting section 11 (21) and the light receiving section 12 (22) in the measurement unit 10 (20). In FIGS. 6 and 7, the arrangement state of the light emitting section 11 and the light receiving section 12 in the measurement unit 10 is illustrated as a representative example.

As illustrated in FIG. 6, an angle between an optical path (also referred to as a "first optical path") Pr1 of light from the light emitting section 11 toward the aperture plane 3s and the normal line 3n of the aperture plane 3s is a first angle θ1. Moreover, an angle between an optical path (also referred to as a "second optical path") Pr2 of light from the aperture plane 3s toward the light receiving section 12 and the normal line 3n of the aperture plane 3s is a second angle θ2. In addition, an angle between the first optical path Pr1 and the second optical path Pr2 is a third angle θ3.

The measurement unit 20 is also in a similar angular relationship among first to third angles θ1 to θ3 to that of the measurement unit 10. Specifically, an angle between a first optical path of light from the light emitting section 21 toward the aperture plane 3s and the normal line 3n of the aperture plane 3s is a first angle θ1. Moreover, an angle between a second optical path of light from the aperture plane 3s toward the light receiving section 22 and the normal line 3n of the aperture plane 3s is a second angle θ2. In addition, an angle between the first and second optical paths is a third angle θ3. That is, each of the first to third angles θ1 to θ3 is the same between the plurality of measurement units 10, 20, and the plurality of measurement units 10, 20 have similar configurations. Thus, measurement conditions are uniformized between the plurality of measurement units 10, 20, and reliability of the evaluation value calculated by the calculation section 73 and the determination result obtained by the determination section 74 is improved.

Moreover, as illustrated in FIGS. 6 and 7, in each of the measurement units 10, 20, the light emitting section 11 and the light receiving section 12 are arranged next to each other. When the third angle θ3 is small, if the sample surface Ss1 irradiated with light by the light emitting section 11 (21) is viewed from the light receiving section 12 (22), contrast on the sample surface Ss1 can be enhanced.

From another point of view, in each of the measurement units 10, 20, the light emitting section 11 and the light receiving section 12 are arranged in a space on one side (a +X side in FIG. 6) of a plane Sv1 perpendicular to both of the aperture plane 3s and an incidence plane Sit including the first optical path Pr1 and the second optical path Pr2. Thus, when the sample surface Ss1 irradiated with light by the light emitting section 11 (21) is viewed from the light receiving section 12 (22), contrast on the sample surface Ss1 is enhanced. Thus, the detection value of the brightness corresponding to the presence or absence of white blurring can be easily obtained. That is, when the third angle θ3 is as small as possible and the first and second angles θ1, θ2 are as close to each other as possible, white blurring can be more reliably determined in the objective manner. Note that it is substantially difficult to set the third angle θ3 to 0° and to completely set the first and second angles θ1, θ2 to the same angle. For these reasons, for example, an aspect is conceivable, in which the third angle θ3 is set to 20°, the first angle θ1 is set to 45°, and the second angle θ2 is set to 65°.

<(2-3) Operation Flow According to Surface Inspection Method>

Figure 8:
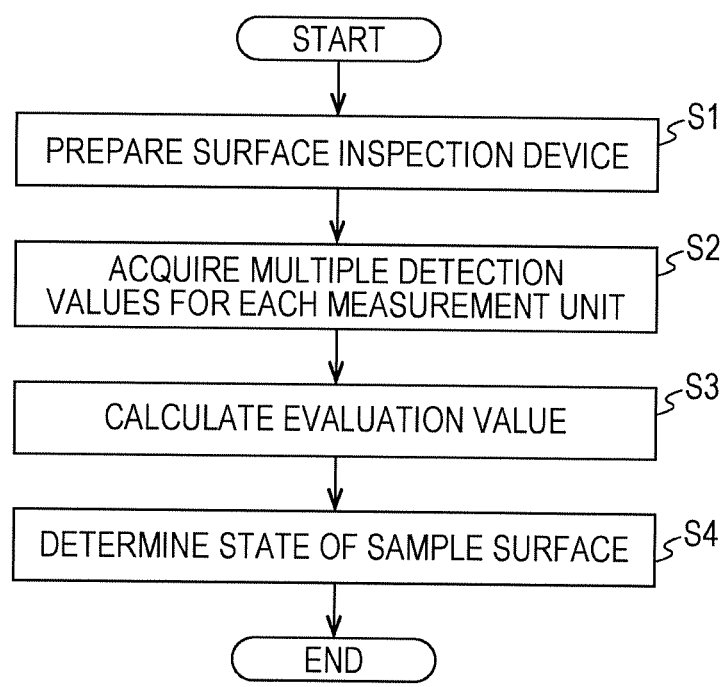
FIG. 8 is a chart of an example of an operation flow of the surface inspection device.

FIG. 8 is a chart of an example of an operation flow according to a surface inspection method using the surface inspection device 100 according to the first embodiment.

First, at step S1, a surface inspection device 100 is prepared. The surface inspection device 100 described herein includes, as described above, an opening 3 and a plurality of measurement units 10, 20, and is configured such that first, second, and third angles θ1, θ2, θ3 are each the same between the plurality of measurement units 10, 20.

At step S2, an acquiring section 72 acquires, for each of the measurement units 10, 20, a detection value of the brightness of light emitted from a sample surface Ss1 in response to light irradiation from a light emitting section 11, 21 via an aperture plane 3s and received by a light receiving section 12, 22 via the aperture plane 3s. In this example, for example, the measurement unit 10 is used such that the sample surface Ss1 is irradiated with light from the light emitting section 11 and that reflected light from the sample surface Ss1 is received by the light receiving section 12. For such reflected light, the detection value (e.g., an L* value) of the brightness is acquired. Moreover, for example, the measurement unit 20 is used such that the sample surface Ss1 is irradiated with light from the light emitting section 21 and that reflected light from the sample surface Ss1 is received by the light receiving section 22. For such reflected light, the detection value (e.g., an L* value) of the brightness is acquired.

At step S3, a calculation section 73 calculates an evaluation value (e.g., a maximum difference $\Delta L^*_{MAX}$) of the degree of variation in the multiple detection values acquired for the plurality of measurement units 10, 20 by the acquiring section 72 at step S2.

At step S4, a determination section 74 determines the state of the sample surface Ss1 based on the evaluation value calculated by the calculation section 73. In this manner, white blurring on the sample surface Ss1 can be determined in an objective manner without variation.

<(2-4) Summary of First Embodiment>

As described above, in the surface inspection device 100 according to the first embodiment, the plurality of measurement units 10, 20 having similar configurations are arranged in different directions with respect to the aperture plane 3s when viewed from above the normal line 3n of the aperture plane 3s. For each of the plurality of measurement units 10, 20, the acquiring section 72 acquires the detection value of the brightness of the sample surface Ss1, the calculation section 73 calculates the evaluation value of the degree of variation in the multiple detection values, and the determination section 74 determines the state of the sample surface Ss1 based on the evaluation value. In this manner, the degree of occurrence of white blurring is not determined in a sensual manner, but can be determined based on the evaluation value in a quantitative manner. As a result, white blurring on the sample surface Ss1 can be determined in the objective manner without variation. Thus, such quantitative and objective determination based on the evaluation value can improve quality management of the resin molded article and the like and stability of the resin molded article and the like in business dealings.

(3) Second Embodiment

In the surface inspection device 100 according to the first embodiment described above, the plurality of measurement units are the two measurement units 10, 20, but the invention is not limited to two units. The plurality of measurement units may include three or more measurement units. A surface inspection device 100A according to a second embodiment including three measurement units 10, 20, 30 will be described herein as a specific example.

Figure 9:
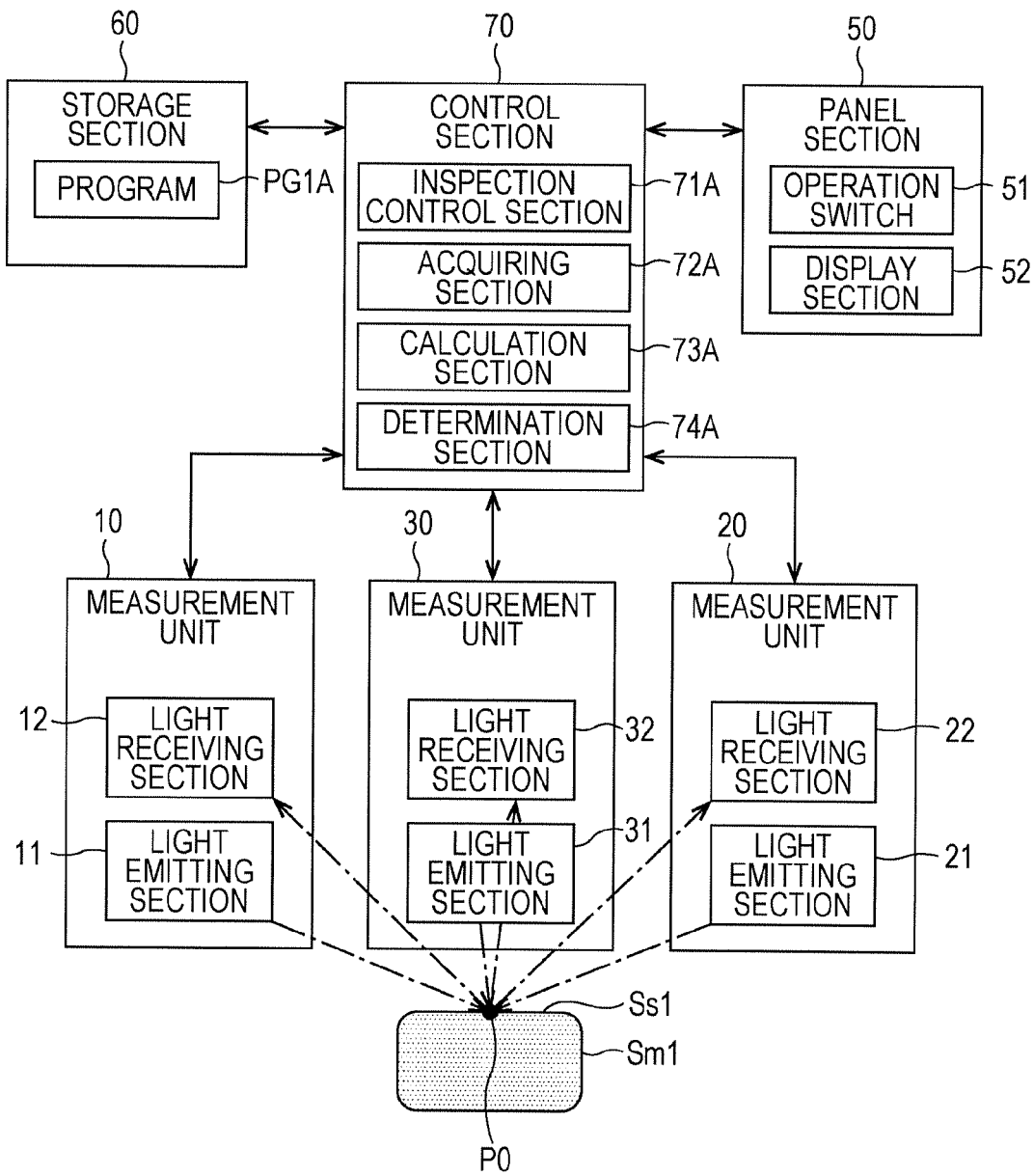
FIG. 9 is a diagram of a functional configuration of a surface inspection device according to a second embodiment.

FIG. 9 is a diagram of a functional configuration of the surface inspection device 100A according to the second embodiment.

The surface inspection device 100A according to the second embodiment is configured such that the measurement unit 30 having a configuration similar to those of the plurality of measurement units 10, 20 is added to the basic surface inspection device 100 according to the first embodiment described above. With such addition, the program PG1 is changed to a different program PG1A, and a functional configuration implemented by the control section 70 is changed. In the surface inspection device 100A, a control section 70 includes, as the functional configuration implemented by reading and execution of the program PG1A, an inspection control section 71A, an acquiring section 72A, a calculation section 73A, and a determination section 74A.

Moreover, light emitting sections 11, 21, 31 are separately provided apart from each other.

Figure 10:
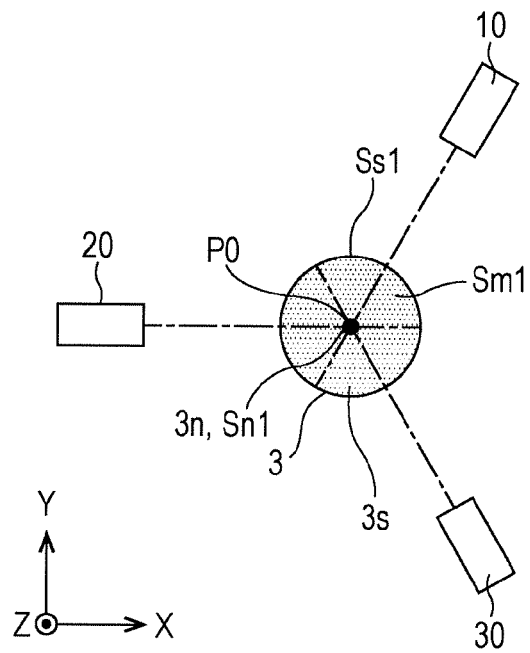
FIG. 10 is a view of an arrangement relationship among three measurement units.

In this example, the plurality of measurement units 10 to 30 are arranged in different directions with respect to an aperture plane 3s when viewed from above a virtual normal line 3n of the aperture plane 3s. For example, as illustrated in FIG. 10, an aspect is conceivable, in which the measurement unit 10, the measurement unit 20, and the measurement unit 30 are in such a relationship that the measurement unit 10, the measurement unit 20, and the measurement unit 30 rotate from each other about the normal line 3n by a predetermined angle (in this example, 120°) set in advance. In light of a characteristic that white blurring is recognizable as viewed from a particular direction, the predetermined angle is set to 120° within a range of equal to or greater than 90°, and a sample surface Ss1 can be evaluated from three directions different from each other to some extent. That is, anisotropy of properties of the sample surface Ss1 can be properly evaluated. This can enhance the accuracy of determination of white blurring.

Moreover, the measurement unit 30 includes the light emitting section 31 and a light receiving section 32. The measurement unit 30 is also in a similar angular relationship among first to third angles $\theta 1$ to $\theta 3$ to those of the measurement units 10, 20.

Specifically, an angle between a first optical path of light from the light emitting section 31 toward the aperture plane 3s and the normal line 3n of the aperture plane 3s is a first angle $\theta 1$, and an angle between a second optical path of light from the aperture plane 3s toward the light receiving section 32 and the normal line 3n of the aperture plane 3s is a second angle $\theta 2$. In addition, an angle between the first and second optical paths is a third angle $\theta 3$. That is, each of the first to third angles $\theta 1$ to $\theta 3$ is the same among the plurality of measurement units 10, 20, 30, and the plurality of measurement units 10, 20, 30 have similar configurations. Thus, measurement conditions are uniformized among the plurality of measurement units 10, 20, 30, and reliability of an evaluation value calculated by the calculation section 73A and a determination result obtained by the determination section 74A is improved.

The inspection control section 71A is configured to cause each of the light emitting sections 11, 21, 31 to sequentially emit light according to user's operation of an operation switch 51, thereby causing the surface inspection device 100A to execute inspection of the sample surface Ss1, for example. Moreover, the inspection control section 71A is configured to display, on a display section 52, at least one of the calculation result obtained by the calculation section 73A or the determination result obtained by the determination section 74A.

The acquiring section 72A is configured to acquire, for each of the measurement units 10, 20, 30, a detection value (e.g., an L* value) of brightness as in the acquiring section 72 according to the first embodiment described above. At this point, as in the measurement units 10, 20, the acquiring section 72A acquires, for the measurement unit 30, the detection value of the brightness of light emitted from the sample surface Ss1 in response to light irradiation from the light emitting section 31 via the aperture plane 3s and received by the light receiving section 32 via the aperture plane 3s.

The calculation section 73A is configured to calculate an evaluation value of the degree of variation in the multiple brightness detection values acquired for the plurality of measurement units 10, 20, 30 by the acquiring section 72A. Such an evaluation value may include, as a first evaluation value, at least one of a difference or a ratio among the multiple detection values of the brightness, for example. This can easily determine white blurring. Moreover, the evaluation value may include, as a second evaluation value, a value indicating a relationship between a representative value of the multiple detection values of the brightness and each detection value of the brightness, for example.

In this example, an aspect is conceivable, in which the representative value of the multiple detection values is, for example, a broad average including, for example, a mere average of the multiple detection values and an average excluding singular values (a maximum value and a minimum value); or a statistical value such as the median of the multiple detection values. In this case, an aspect is conceivable, in which the second evaluation value is, for example, a maximum value of a difference between each detection value of the brightness and the representative value of the multiple detection values. For example, in the case of using the average as the representative value, an aspect is conceivable, in which the difference between each detection value of the brightness and the representative value of the multiple detection values is a deviation for each detection value of the brightness and a maximum value of such a deviation is calculated as the second evaluation value. In this example, when the detection value is the L* value, the average may be the average of the L* values, the deviation for each detection value may be a difference between the average $L^*_{MEAN}$ of the L* values and each L* value, and the second evaluation value may be a maximum value (also referred to as a "maximum deviation") of the deviations for the detection values.

As in the determination section 74 according to the first embodiment described above, the determination section 74A is configured to determine the state of the sample surface Ss1 based on the evaluation value calculated by the calculation section 73A. In this manner, white blurring can be determined in an objective manner without variation. In the determination section 74A, the state of the sample surface Ss1 is determined by comparison between the evaluation value and a preset reference value, for example. In this example, determination (also referred to as "first determination") of the state of the sample surface Ss1 by comparison between the first evaluation value and a first reference value and determination (also referred to as "second determination") of the state of the sample surface Ss1 by comparison between the second evaluation value and a second reference value are performed, for example. This can easily determine white blurring in the objective manner without variation. Note that either one of the first or second determination may be performed. Note, however, that when the second determination is performed, anisotropy of reflection properties of the sample surface Ss1 can be more properly evaluated, and therefore, white blurring can be more reliably determined in the objective manner.

For example, as in the first embodiment described above, the first evaluation value may be a maximum difference $\Delta L^*_{MAX}$ and the first reference value may be 1.2. In this case, when the maximum difference $\Delta L^*_{MAX}$ exceeds a first reference value of 1.2, it is determined that there is white blurring on the sample surface Ss1. Moreover, as in the first embodiment described above, a first auxiliary reference value may be set for the first reference value. For example, when the first auxiliary reference value is 0.8 and the maximum difference $\Delta L^*_{MAX}$ is greater than 0.8 and equal to or less than 1.2, it is determined that white blurring is suspected of being caused.

Moreover, the second evaluation value may be the maximum deviation for the L* value, and the second reference value may be 1.2 as in the first reference value. In this case, when the maximum deviation for the L* value exceeds a second reference value of 1.2, there is a certain amount of great difference in the brightness of the sample surface Ss1 depending on the direction of irradiating the sample surface Ss1 with particular light, and therefore, it is determined that there is white blurring on the sample surface Ss1. Note that the first and second reference values can be, for example, set according to a sensory evaluation result by together performing calculation of the maximum difference $\Delta L^*_{MAX}$ and the maximum deviation for the L* value by using the surface inspection device 100A or a configuration or a simulation similar to the surface inspection device 100A and sensory evaluation on the presence of white blurring by visual checking of the sample surface Ss1. That is, the first and second reference values can be set according to an allowable degree of white blurring. Moreover, as in the first reference value, a second auxiliary reference value may be also set for the second reference value. For example, when the second auxiliary reference value is 0.8 and the maximum deviation for the L* value is greater than 0.8 and equal to or less than 1.2, it is determined that white blurring is suspected of being caused.

Figure 11:
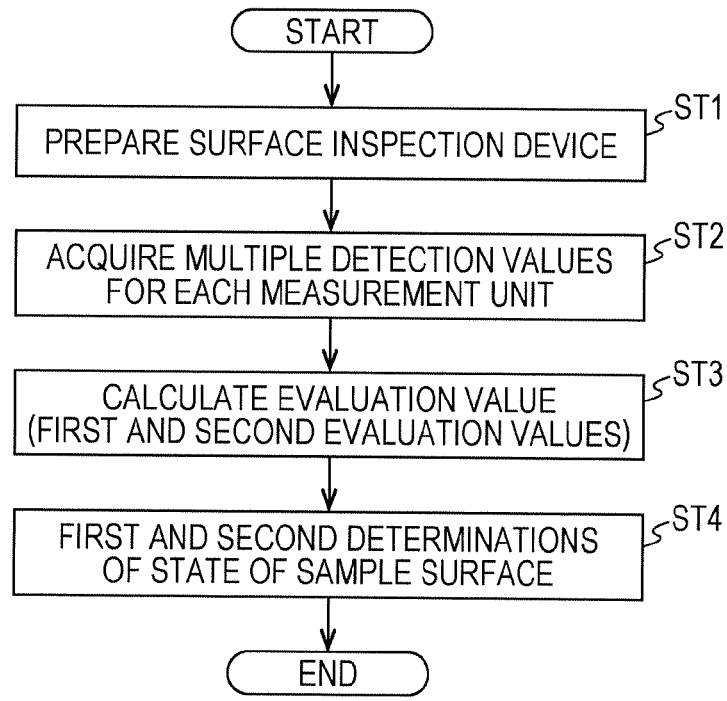
FIG. 11 is a chart of an example of an operation flow of the surface inspection device.

FIG. 11 is a chart of an example of an operation flow according to a surface inspection method using the surface inspection device 100A according to the second embodiment.

First, at step ST1, a surface inspection device 100A is prepared. The surface inspection device 100A described herein includes, as described above, an opening 3 and a plurality of measurement units 10, 20, 30, and is configured such that first, second, and third angles θ1, θ2, θ3 are each the same between the plurality of measurement units 10, 20, 30.

At step ST2, an acquiring section 72A acquires, for each of the measurement units 10, 20, 30, a detection value of the brightness of light emitted from a sample surface Ss1 in response to light irradiation from a light emitting section 11, 21, 31 via an aperture plane 3s and received by a light receiving section 12, 22, 32 via the aperture plane 3s. In this example, for example, the measurement unit 10 is used such that the sample surface Ss1 is irradiated with light from the light emitting section 11 and that reflected light from the sample surface Ss1 is received by the light receiving section 12. For such reflected light, the detection value (e.g., an L* value) of the brightness is acquired. Moreover, for example, the measurement unit 20 is used such that the sample surface Ss1 is irradiated with light from the light emitting section 21 and that reflected light from the sample surface Ss1 is received by the light receiving section 22. For such reflected light, the detection value (e.g., an L* value) of the brightness is acquired. Further, for example, the measurement unit 30 is used such that the sample surface Ss1 is irradiated with light from the light emitting section 31 and that reflected light from the sample surface Ss1 is received by the light receiving section 32. For such reflected light, the detection value (e.g., an L* value) of the brightness is acquired.

At step ST3, a calculation section 73A calculates an evaluation value (e.g., first and second evaluation values) of the degree of variation in the multiple detection values acquired for the plurality of measurement units 10, 20, 30 at step ST2. In this example, a maximum difference $\Delta L^*_{MAX}$ as the first evaluation value is calculated, and a maximum deviation for the L* value as the second evaluation value is calculated.

At step ST4, a determination section 74A determines (first and second determinations) the state of the sample surface Ss1 based on the evaluation values calculated by the calculation section 73A. In this example, when the maximum difference $\Delta L^*_{MAX}$ as the first evaluation value exceeds, for example, a first reference value of 1.2 in the first determination, it is determined that there is white blurring. Moreover, in the first determination, when the maximum difference $\Delta L^*_{MAX}$ is greater than a first auxiliary reference value of 0.8 and equal to or less than 1.2, it is determined that white blurring is suspected of being caused. Further, when the maximum deviation for the L* value as the second evaluation value exceeds, for example, a second reference value of 1.2 in the second determination, it is determined that there is white blurring. In addition, in the second determination, when the maximum deviation is greater than a second auxiliary reference value of 0.8 and equal to or less than 1.2, it is determined that white blurring is suspected of being caused.

As described above, in the surface inspection device 100A according to the second embodiment, the detection value of the brightness of the sample surface Ss1 is acquired by the acquiring section 72A for each of three or more measurement units 10, 20, 30 having similar configurations and arranged in different directions with respect to the aperture plane 3s when viewed from above the normal line 3n of the aperture plane 3s. Then, the calculation section 73A calculates the second evaluation value of the degree of variation in the multiple detection values, and the determination section 74A determines the state of the sample surface Ss1. In this manner, white blurring can be more reliably determined in the objective manner.

(4) Third Embodiment

In the surface inspection devices 100, 100A according to the first and second embodiments described above, the plurality of light emitting sections 11, 21, 31 included respectively in the plurality of measurement units 10, 20, 30 are separately provided, but the invention is not limited to such a configuration. For example, a plurality of light emitting sections included respectively in a plurality of measurement units may be in an integrated light emitting region. That is, a configuration may be employed, which has a single light emitting region and a plurality of light receiving sections. With this configuration, multiple detection values can be obtained by a single time of lightening of the light emitting region. Thus, white blurring can be promptly determined, for example.

In this example, when the plurality of light receiving sections included respectively in the plurality of measurement units are arranged in a relationship of rotational symmetry about a normal line 3n of an aperture plane 3s and the integrated light emitting region is disposed in a relationship of rotational symmetry about the normal line 3n, measurement conditions are the same among the plurality of measurement units 10d, 20d, 30d. As a result, reliability of an evaluation value calculated by a calculation section 73 and a determination result obtained by a determination section 74 can be improved.

In this example, a surface inspection device 100B according to a third embodiment having three measurement units 10d to 30d will be described as a specific example.

Figure 12:
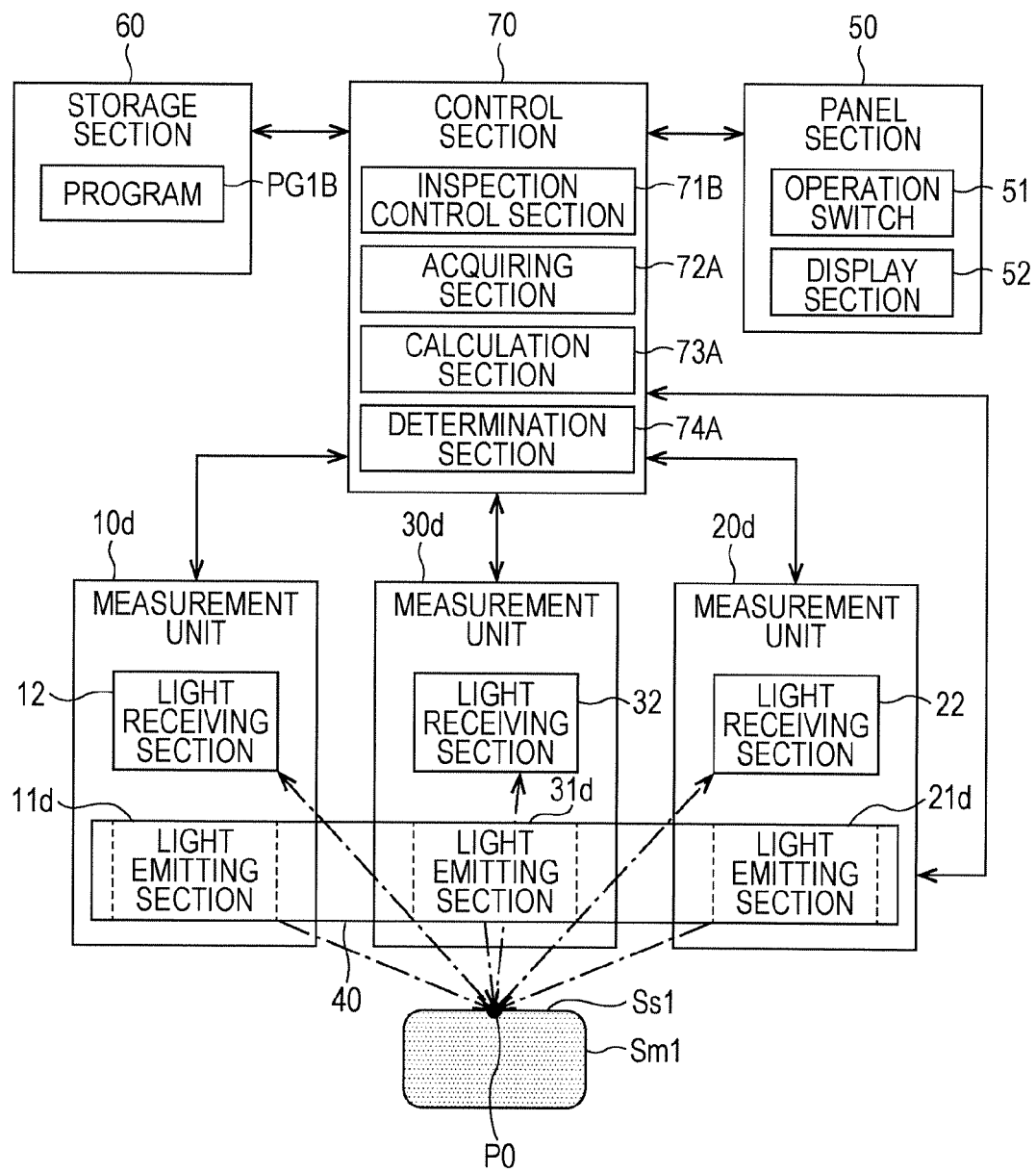
FIG. 12 is a diagram of a function configuration of a surface inspection device according to a third embodiment.

FIG. 12 is a diagram of a functional configuration of the surface inspection device 100B according to the third embodiment.

The surface inspection device 100B according to the third embodiment is configured based on the surface inspection device 100A according to the second embodiment described above such that the light emitting sections 11, 21, 31 are changed to light emitting sections 11d, 21d, 31d included in an integrated light emitting region 40 to replace the measurement units 10, 20, 30 with the measurement units 10d, 20d, 30d. The light emitting region 40 may be configured to have a single light source or a group of a plurality of light sources, for example. The light emitting sections 11d, 21d, 31d each form a portion of the light emitting region 40. Note that with a change of the light emitting sections 11, 21, 31 to the light emitting sections 11d, 21d, 31d included in the integrated light emitting region 40, the program PG1A is changed to a different program PG1B, and the inspection control section 71A as the functional configuration implemented by the control section 70 is changed to an inspection control section 71B.

The inspection control section 71B is configured to cause the light emitting region 40 to emit light according to user's operation of an operation switch 51, thereby causing the surface inspection device 100B to execute inspection of a sample surface Ss1, for example. Moreover, the inspection control section 71B is configured to display, on a display section 52, a determination result obtained by the determination section 74A.

FIG. 13 is a view of an example of an arrangement relationship among the light emitting region 40 and the plurality of measurement units 10d, 20d, 30d. As illustrated in FIG. 13, the light emitting region 40 has a circular ring shape about a normal line 3n of an aperture plane 3s, for example. Of the light emitting region 40, a first portion may form the light emitting section 11d of the measurement unit 10d, a second portion may form the light emitting section 21d of the measurement unit 20d, and a third portion may form the light emitting section 31d of the measurement unit 30d. Moreover, in this example, an aspect is conceivable, in which the normal line 3n of the aperture plane 3s, the light emitting sections 11d, 21d, 31d, and light receiving sections 12, 22, 23 are, in each of the measurement units 10d, 20d, 30d, in an angular relationship among first to third angles θ1 to θ3 as in the measurement units 10, 20, 30 according to the second embodiment described above. Thus, measurement conditions are uniformized among the plurality of measurement units 10d, 20d, 30d.

(5) Specific Examples

Specific examples will be described, in which the surface inspection device 100 according to the first embodiment described above and the surface inspection device 100A according to the second embodiment described above were used to inspect the presence or absence of white blurring on the sample surface Ss1 of the sample Sm1.

In these examples, the sample Sm1 was a polypropylene resin molded article having an embossed portion. This polypropylene resin molded article was produced in a colored state in such a manner that polypropylene is molten and molded after being mixed with pellet grains. Moreover, as illustrated in FIG. 14, a first region Ar1 for which the presence of white blurring has been confirmed by sensory evaluation by visual checking and second and third regions Ar2, Ar3 for which the presence of white blurring has not been confirmed were used as targets for inspection.

For both of the surface inspection devices 100, 100A, the first angle θ1 was set to 45°, the second angle θ2 was set to 65°, and the third angle θ3 was set to 20°. That is, the first optical path Pr1 and the second optical path Pr2 are arranged along the same virtual plane including the normal line 3n of the aperture plane 3s.

In the surface inspection device 100 according to the first embodiment, the acquiring section 72 acquired, for each of the measurement units 10, 20, the L* value as the detection value of the brightness of light emitted from the sample surface Ss1 in response to light irradiation from the light emitting section 11, 21 via the aperture plane 3s and received by the light receiving section 12, 22 via the aperture plane 3s. Next, the calculation section 73 calculated the maximum difference $\Delta L^*_{MAX}$ as the evaluation value of the degree of variation in the multiple L* values acquired for the plurality of measurement units 10, 20. Then, the determination section 74 determined the state (the presence or absence of white blurring) of the sample surface Ss1 based on the evaluation value calculated by the calculation section 73. The reference value in this determination was set to 1.2. Moreover, the auxiliary reference value was set to 0.8.

Moreover, in the surface inspection device 100A according to the second embodiment, the acquiring section 72A acquired, for each of the measurement units 10, 20, 30, the L* value as the detection value of the brightness of light emitted from the sample surface Ss1 in response to light irradiation from the light emitting section 11, 21, 31 via the aperture plane 3s and received by the light receiving section 12, 22, 32 via the aperture plane 3s. Next, the calculation section 73A calculated the maximum difference $\Delta L^*_{MAX}$ as the first evaluation value of the degree of variation in the multiple L* values acquired for the plurality of measurement units 10, 20, 30 and the maximum deviation for the L* value as the second evaluation value. Then, the determination section 74A performed the first determination of the state (the presence or absence of white blurring) of the sample surface Ss1 based on the first evaluation value calculated by the calculation section 73A, and performed the second determination of the state (the presence or absence of white blurring) of the sample surface Ss1 based on the second evaluation value calculated by the calculation section 73A.

FIGS. 15 to 17 are tables of an example of the inspection results obtained by the surface inspection device 100 according to the first embodiment. FIG. 15 shows the inspection results targeted for the first region Ar1, FIG. 16 shows the inspection results targeted for the second region Art, and FIG. 17 shows the inspection results targeted for the third region Ar3. Specifically, FIGS. 15 to 17 sequentially show the L* value as the detection value for each of the measurement units 10, 20, the maximum differences $\Delta L^*_{MAX}$ as the evaluation values, and the determination results.

Moreover, FIGS. 18 to 20 are tables of an example of the inspection results obtained by the surface inspection device 100A according to the second embodiment. FIG. 18 shows the inspection results targeted for the first region Ar1, FIG. 19 shows the inspection results targeted for the second region Ar2, and FIG. 20 shows the inspection results targeted for the third region Ar3. Specifically, FIGS. 18 to 20 sequentially show the L* value as the detection value for each of the measurement units 10, 20, 30, the maximum difference $\Delta L^*_{MAX}$ as the first evaluation value, the results of the first determination, the average $L^*_{MEAN}$ of the L* values, the deviation for the L* values for each of the measurement units 10, 20, 30, the maximum deviation for the L* value, and the results of the second determination.

For the first region Ar1, any of the surface inspection devices 100, 100A obtained the evaluation value exceeding the reference value, and it was determined that there is white blurring, as illustrated in FIGS. 15 and 18. For the second region Ar2, any of the surface inspection devices 100, 100A obtained the evaluation value not exceeding the reference value and the auxiliary reference value, and it was determined that there is no white blurring, as illustrated in FIGS. 16 and 19. Note that for the first region Ar1, the direction in which the measurement unit 20 corresponding to the L* value as the highest detection value is disposed and the direction of an observer when it was determined that there is white blurring in a sensory test by visual checking are coincident with each other, and the maximum difference $\Delta L^*_{MAX}$ and the deviation for the L* value also showed tendency similar to that of the results of the sensory test by visual checking.

For the third region Ar3 for which no white blurring has been observed in the sensory test by visual checking, the determination by the surface inspection device 100 and the first determination by the surface inspection device 100A determined that white blurring is suspected of being caused, as illustrated in FIGS. 17 and 20. On the other hand, as illustrated in FIG. 20, the second determination by the surface inspection device 100A determined that there is no white blurring.

A phenomenon leading to different results between the first and second determinations as described above was considered as being caused due to properties (also referred to as "aeolotropy" or "anisotropy") that microscopic reflection properties of the sample surface Ss1 having the embossed portion vary according to directions. Specifically, in the case of simple evaluation based on the difference (the maximum difference $\Delta L^*_{MAX}$) between the maximum value and the minimum value of the L* value as the inspection value, even when no white blurring has been actually observed, it might be considered that the maximum difference $\Delta L^*_{MAX}$ for the brightness exceeds the reference value. For such a phenomenon, as long as the deviations for three or more L* values of the brightness are evaluated as in the second determination by the surface inspection device 100A, a singular measurement direction showing brightness greatly different from those of other measurement directions is specified. Thus, it was assumed that influence of the anisotropy of the reflection properties of the sample surface Ss1 is excluded as much as possible from the measurement results and therefore, occurrence and influence of white blurring can be more reliably determined in the objective manner.

(6) Variations

Note that the invention is not limited to the above-described first to third embodiments, and various changes, modifications, and the like can be made without departing from the gist of the invention.

For example, in the above-described first and second embodiments, the light emitting sections 11, 21, 31 each have the light source, but the invention is not limited to such a configuration. For example, the light emitting sections 11, 21, 31 may be configured to emit light guided by a light guide unit after being emitted from a common light source. Examples of the light guide unit include a mirror, an optical fiber, and the like configured to reflect light. In the case of employing such a configuration, for example, a shutter configured to block light is openably provided on an optical path extending from the light source to the sample surface Ss1 via each of the light emitting sections 11, 21, 31 so that the sample Sm1 can be selectively irradiated with light from any one of the light emitting sections 11, 21, 31.

In the above-described first to third embodiments, the light receiving sections 12, 22, 32 each have the light detection unit, but the invention is not limited to such a configuration. For example, each of the light receiving sections 12, 22, 32 does not necessarily include the light detection unit, and may be configured to guide received light toward a common light detection unit via a light guide unit. In this case, for example, a front most surface of an optical system such as a collimate lens and an optical fiber is employed as the light receiving sections 12, 22, 32. Examples of the light guide unit include a mirror, an optical fiber, and the like configured to reflect light. In the case of employing such a configuration, for example, a shutter configured to block light is openably provided on an optical path extending from the sample surface Ss1 to the light detection unit via each of the light receiving sections 12, 22, 32 so that light can enter the light detection unit from any one of the light receiving sections 12, 22, 32.

In the above-described first to third embodiments, the inspection control section 71 visually outputs, to the display section 52, the determination result obtained by the determination section 74. However, the invention is not limited to such a configuration. For example, the inspection control section 71 may visually output, to the display section 52, at least one of the calculation result obtained by the calculation section 73 or the determination result obtained by the determination section 74. For example, in the case where the evaluation value as the calculation result obtained by the calculation section 73 is visually output to the display section 52, when a user recognizes the reference value for comparison with the evaluation value, white blurring can be determined in the objective manner without variation. Alternatively, in the surface inspection devices 100, 100A, 100B, at least one type of data of the evaluation value or the determination result may be output to external equipment without being visually displayed. That is, at least one type of data of the evaluation value or the determination result may be output.

In the above-described first to third embodiments, the L* value is employed as the detection value of the brightness, but the invention is not limited to such a value. For example, a value of the brightness of another color such as a Y-value of the XYZ color coordinate system may be taken as the detection value of the brightness. Alternatively, for example, the reflectance of light with a particular wavelength (a wavelength of around 550 nm) on the sample surface Ss1 may be employed as the detection value of the brightness.

In the above-described second and third embodiments, the maximum value (e.g., the maximum value of the L* value) of the deviation for the detection value (e.g., the L* value) of the brightness is employed as the second evaluation value, but the invention is not limited to such a value. For example, a maximum value or a minimum value of a ratio between the average of the detection values (e.g., the L* values) and each detection value may be employed as the second evaluation value. The "ratio" described herein includes, for example, a value obtained by dividing each detection value by the average of the multiple detection values or a value obtained by dividing the average of the multiple detection values by each detection value.

In the above-described first to third embodiments, the light emitting section 11, 21, 31 (11d, 21d, 31d) and the light receiving section 12, 22, 32 are arranged next to each other in each of the measurement units 10, 20, 30 (10d, 20d, 30d), and the third angle θ3 is set to a small angle. However, the invention is not limited to such a configuration. For example, in each of the measurement units 10, 20, 30 (10d, 20d, 30d), as long as the angular relationship among the aperture plane 3s, the light emitting sections 11, 21, 31 (11d, 21d, 31d), and the light receiving sections 12, 22, 32 can be substantially held constant, the light emitting section 11, 21, 31 (11d, 21d, 31d) and the light receiving section 12, 22, 32 are not necessarily arranged next to each other, but may be arranged apart from each other to some extent.

In the above-described first to third embodiments, adjacent ones of the measurement units are in such a relationship that these units rotate from each other about the normal line 3n of the aperture plane 3s by equal to or greater than 90°, but the invention is not limited to such a configuration. For example, an aspect may be employed, in which any two of the plurality of measurement units are in such a relationship that these two units rotate from each other about the normal line 3n of the aperture plane 3s by equal to or greater than 90°.

In the above-described first to third embodiments, the presence or absence of white blurring on the sample surface Ss1 is targeted for evaluation and determination, but the invention is not limited to such a configuration. For example, the state of the sample surface Ss1 leading to anisotropy of brightness other than white blurring may be targeted for evaluation and determination.

Note that all or part of the configuration of each of the above-described first to third embodiments and the variations thereof can be, needless to say, optionally combined without inconsistencies.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST 2 device body
3 opening
3n normal line
3s aperture plane
10, 10d, 20, 20d, 30, 30d measurement unit
11, 11d, 21, 21d, 31, 31d light emitting section
12, 22, 32 light receiving section
40 light emitting region
50 operation display section
60 storage section
70 control section
71, 71A, 71B inspection control section
72, 72A acquiring section
73, 73A calculation section
74, 74A determination section
100, 100A, 100B surface inspection device
PG1, PG1A, PG1B program
Pr1 first optical path
Pr2 second optical path
Si1 incidence plane
Sm1 sample
Ss1 sample surface

The invention claimed is:
1. A surface inspection device for inspecting a sample surface, comprising:
  an opening defining an aperture plane;
  a plurality of optical transceivers, each comprising a light emitter and a light receiver that are arranged in different directions with respect to the aperture plane when viewed from above a virtual normal line of the aperture plane;

a processor that:

acquires a plurality of detection values, each generated by a different optical transceiver of the plurality of optical transceivers and each specifying a brightness of light emitted from the sample surface in response to light irradiation by an optical transceiver of the plurality of optical transceivers via the aperture plane and received by the optical transceiver that irradiated the sample surface via the aperture plane; and calculates an evaluation value of a degree of variation between the detection values of the plurality of detection values, wherein a first angle between a first optical path of light, from a light emitter of a first optical transceiver of the plurality of optical transceivers, toward the aperture plane and the normal line of the aperture plane, a second angle between a second optical path of light from the aperture plane toward the a light receiver of the first optical transceiver and the normal line, and a third angle between the first and second optical paths are equal among the plurality of optical transceivers.

2. The surface inspection device according to claim 1, wherein
the light emitters of the plurality of optical transceivers are physically separated from one another.

3. The surface inspection device according to claim 1, wherein
each light emitter of each of the plurality of optical transceivers is disposed in an integrated light emitting region.

4. The surface inspection device according to claim 1, wherein
the evaluation value comprises at least one selected from either a difference or a ratio between the plurality of detection values.

5. The surface inspection device according to claim 1, wherein
the processor determines a state of the sample surface based on the evaluation value.

6. The surface inspection device according to claim 5, wherein
the processor determines the state of the sample surface by comparing the evaluation value and a preset reference value.

7. The surface inspection device according to claim 1, wherein
the light emitter and the light receiver of each of the plurality of optical transceivers are arranged in a space on one side of a plane perpendicular to both of the aperture plane and an incidence plane comprising the first and second optical paths.

8. The surface inspection device according to claim 1, wherein
the plurality of optical transceivers comprises three optical transceivers, and
the evaluation value comprises a value indicating a relationship between a representative value of the plurality of detection values and each of the plurality of detection values.

9. A surface inspection method comprising:

a) a step of preparing a surface inspection device provided with an opening defining an aperture plane, wherein the surface inspection device comprises a plurality of optical transceivers, each comprising a light emitter and a light receiver that are arranged in different directions with respect to the aperture plane when viewed from above a virtual normal line of the aperture plane, and wherein a first angle between a first optical path of light, from the light emitter of a first optical transceiver of the plurality of optical transceivers, toward the aperture plane and the virtual normal line of the aperture plane, a second angle between a second optical path of light from the aperture plane toward a light receiver of the first optical transceiver and the normal line, and a third angle between the first and second optical paths are equal among the plurality of optical transceivers;

(b) a step of acquiring a plurality of detection values, each generated by a different optical transceiver of the plurality of optical transceivers and each specifying a brightness of light emitted from the sample surface in response to light irradiation by an optical transceiver of the plurality of optical transceivers via the aperture plane and received by the optical transceiver that light irradiated the sample surface, via the aperture plane; and (c) a step of calculating an evaluation value of a degree of variation between the detection values of the plurality of detection values.

10. A non-transitory recording medium storing a computer readable program for causing a surface inspection device to function as the surface inspection device according to claim 1 by execution by the processor of the surface inspection device.

11. The surface inspection device according to claim 2, wherein
the evaluation value comprises at least one selected from either a difference or a ratio between the plurality of detection values.

12. The surface inspection device according to claim 2, wherein
the processor determines a state of the sample surface based on the evaluation value.

13. The surface inspection device according to claim 2, wherein
the light emitter section and the light receiver of each of the plurality of optical transceivers are arranged in a space on one side of a plane perpendicular to both of the aperture plane and an incidence plane including the first and second optical paths.

14. The surface inspection device according to claim 2, wherein
the plurality of optical transceivers comprises at least three optical transceivers, and
the evaluation value comprises a value indicating a relationship between a representative value of the plurality of detection values and each of the plurality of detection values.

15. A non-transitory recording medium storing a computer readable program for causing a surface inspection device to function as the surface inspection device according to claim 2 by execution by the processor of the surface inspection device.

16. The surface inspection device according to claim 3, wherein
the evaluation value comprises either a difference or a ratio between the plurality of detection values.

17. The surface inspection device according to claim 3, wherein
the processor determines a state of the sample surface based on the evaluation value.

18. The surface inspection device according to claim 3, wherein
- the light emitter and the light receiver of each of the plurality of optical transceivers are arranged in a space on one side of a plane perpendicular to both of the aperture plane and an incidence plane including the first and second optical paths.

19. The surface inspection device according to claim 3, wherein
- the plurality of optical transceivers comprises at least three optical transceivers, and
- the evaluation value comprises a value indicating a relationship between a representative value of the plurality of detection values and each of the plurality of detection values.

20. A non-transitory recording medium storing a computer readable program for causing a surface inspection device to function as the surface inspection device according to claim 3 by execution by the processor of the surface inspection device.

* * * * *